United States Patent
Vollmann et al.

(10) Patent No.: US 11,427,504 B2
(45) Date of Patent: Aug. 30, 2022

(54) METHOD TO PRODUCE A DENTAL STRUCTURE AND DENTAL STRUCTURE

(71) Applicant: DENTSPLY SIRONA Inc., York, PA (US)

(72) Inventors: Markus Vollmann, Gelnhausen (DE); Udo Schusser, Alzenau (DE)

(73) Assignee: DENTSPLY SIRONA INC., York, PA (US)

( * ) Notice: Subject to any disclaimer, the term of this patent is extended or adjusted under 35 U.S.C. 154(b) by 155 days.

(21) Appl. No.: 15/159,427

(22) Filed: May 19, 2016

(65) Prior Publication Data

US 2016/0340240 A1    Nov. 24, 2016

(30) Foreign Application Priority Data

May 22, 2015   (DE) .................... 10 2015 108 178.4

(51) Int. Cl.
| | |
|---|---|
| *C03C 21/00* | (2006.01) |
| *A61C 13/083* | (2006.01) |
| *A61C 5/77* | (2017.01) |
| *A61C 13/08* | (2006.01) |
| *C03C 4/00* | (2006.01) |

(Continued)

(52) U.S. Cl.
CPC .............. *C03C 21/008* (2013.01); *A61C 5/77* (2017.02); *A61C 13/081* (2013.01); *A61C 13/083* (2013.01); *A61K 6/818* (2020.01); *A61K 6/822* (2020.01); *A61K 6/833* (2020.01); *A61K 6/853* (2020.01); *C03C 3/097* (2013.01);

(Continued)

(58) Field of Classification Search
CPC . C03C 21/002; C03C 10/0027; A61C 13/081; A61K 6/0273
See application file for complete search history.

(56) References Cited

U.S. PATENT DOCUMENTS 2,682,092 A * 6/1954 Henricks .................... B22C 1/18
    264/117
3,357,876 A * 12/1967 Rinehart ............... C03C 21/002
    501/63

(Continued)

FOREIGN PATENT DOCUMENTS

| CA | 2892284 A1 | 6/2014 |
| CH | 668699 A5 | 1/1989 |

(Continued)

OTHER PUBLICATIONS

I.L. Denry et. al., Enhanced Chemical Strengthening of Feldspathic Dental Porcelain, J Dent Res; Oct. 1993; pp. 1429-1433.

(Continued)

*Primary Examiner* — Jodi C Franklin
(74) *Attorney, Agent, or Firm* — Dentsply Sirona Inc.

(57) ABSTRACT

The invention relates to a method to produce a dental structure with a cavity having a negative form of the structure, which is formed in an investment material, wherein flowable lithium silicate glass ceramic is pressed into the cavity. Thereby a compressive surface stress is created in the ceramic structure through the replacement of lithium ions by alkali ions, in that the model is enriched with alkali compounds and/or the model is covered with a layer of a material containing alkali ions.

8 Claims, 3 Drawing Sheets

(51) Int. Cl.
*C03C 3/097* (2006.01)
*A61K 6/818* (2020.01)
*A61K 6/822* (2020.01)
*A61K 6/833* (2020.01)
*A61K 6/853* (2020.01)
*C03C 10/00* (2006.01)

(52) U.S. Cl.
CPC ........ *C03C 4/0021* (2013.01); *C03C 10/0027* (2013.01); *C03C 21/002* (2013.01); *C03C 2204/00* (2013.01)

(56) References Cited

U.S. PATENT DOCUMENTS

| | | | | |
|---|---|---|---|---|
| 3,608,051 A * | 9/1971 | Scott | ............... | B28B 7/342 264/261 |
| 3,610,317 A * | 10/1971 | Benfield | ............... | B22C 9/04 164/249 |
| 3,620,508 A * | 11/1971 | Lea | ............... | B22C 15/12 366/108 |
| 3,631,745 A * | 1/1972 | Walkey | ............... | B21D 37/20 264/225 |
| 3,632,321 A * | 1/1972 | Plumat | ............... | C03C 21/00 204/199 |
| 3,730,871 A * | 5/1973 | Boffe | ............... | C03C 21/001 204/245 |
| 3,804,643 A * | 4/1974 | Arita | ............... | B22C 1/188 106/38.3 |
| 3,963,818 A * | 6/1976 | Sakoda | ............... | B22C 9/105 264/109 |
| 4,078,029 A * | 3/1978 | Yoshida | ............... | C04B 28/24 264/225 |
| 4,108,934 A * | 8/1978 | Rubens | ............... | B29C 44/445 264/53 |
| 4,290,793 A * | 9/1981 | Brockway | ............... | C03C 23/00 65/114 |
| 4,351,757 A * | 9/1982 | Hoeschele | ............... | C08K 5/09 524/169 |
| 4,546,006 A * | 10/1985 | Ohno | ............... | C04B 41/85 106/35 |
| 4,647,311 A * | 3/1987 | Ohi | ............... | A61K 6/0625 106/35 |
| 4,766,948 A * | 8/1988 | Behr | ............... | B22D 27/20 106/38.22 |
| 4,784,606 A | 11/1988 | Jones | | |
| 4,927,673 A * | 5/1990 | Buntrock | ............... | B28B 7/342 427/397.8 |
| 5,232,481 A * | 8/1993 | Johnston | ............... | C03C 21/002 65/30.13 |
| 5,535,810 A * | 7/1996 | Compton | ............... | A61F 2/30767 164/35 |
| 5,795,151 A * | 8/1998 | Nonami | ............... | A61K 6/836 501/100 |
| 6,484,791 B1 * | 11/2002 | Vidal | ............... | A61C 13/20 164/113 |
| 7,892,995 B2 * | 2/2011 | Castillo | ............... | A61K 6/0235 106/35 |
| 8,685,294 B2 * | 4/2014 | Fecher | ............... | A61C 13/0004 264/19 |
| 2002/0022563 A1 * | 2/2002 | Schweiger | ............... | A61K 6/818 106/35 |
| 2003/0073563 A1 * | 4/2003 | Brodkin | ............... | C03C 4/0021 106/35 |
| 2003/0198838 A1 * | 10/2003 | Petticrew | ............... | A61C 13/20 428/701 |
| 2005/0098064 A1 * | 5/2005 | Schweiger | ............... | C03C 10/0027 106/35 |
| 2009/0000473 A1 * | 1/2009 | Davis | ............... | C03B 32/02 95/55 |
| 2010/0214788 A1 * | 8/2010 | Kadono | ............... | G02B 6/005 428/141 |
| 2011/0256409 A1 * | 10/2011 | Ritzberger | ............... | A61K 6/0215 428/432 |
| 2011/0293942 A1 * | 12/2011 | Cornejo | ............... | C03C 3/083 428/410 |
| 2013/0189486 A1 * | 7/2013 | Wang | ............... | C03C 21/002 501/63 |
| 2013/0274085 A1 * | 10/2013 | Beall | ............... | C03B 20/00 65/33.1 |
| 2013/0295523 A1 * | 11/2013 | Durschang | ............... | C03C 3/097 433/212.1 |
| 2014/0083326 A1 * | 3/2014 | Mori | ............... | A61K 6/0625 106/35 |
| 2014/0331716 A1 * | 11/2014 | Ahmed | ............... | C03C 21/002 703/1 |
| 2015/0104655 A1 | 4/2015 | Kim | | |
| 2017/0366520 A1 * | 12/2017 | Templin | ............... | H04L 9/3268 |
| 2022/0149372 A1 * | 5/2022 | Xie | ............... | H01M 4/131 |
| 2022/0153629 A1 * | 5/2022 | Burger | ............... | C03C 21/002 |

FOREIGN PATENT DOCUMENTS

| | | |
|---|---|---|
| DE | 3015529 A1 | 11/1980 |
| EP | 2062665 A1 | 5/2009 |
| GB | 1255942 A | 11/1971 |

OTHER PUBLICATIONS

R.R. Seghi et. al., Effects of Ion Exchange on Hardness and Fracture Toughness of Dental Ceramics, The International Journal of Prosthodontics, vol. 5, No. 4, 1992; pp. 309-314.

International Search Report; PCT/EP2016/061403; dated Jul. 20, 2017, 4 pages.

Written Opinion of the International Searching Authority; PCT/EP2016/061403; dated Jul. 20, 2017, 7 pages.

International Preliminary Report on Patentability; PCT/EP2016/061403; dated Jul. 20, 2017, 15 pages.

* cited by examiner

METHOD TO PRODUCE A DENTAL STRUCTURE AND DENTAL STRUCTURE

THE CROSS-REFERENCE TO RELATED APPLICATIONS

This patent application claims the benefit of and priority to German Patent Application No. 10 2015 108 178.4, filed on May 22, 2015, which is herein incorporated by reference for all purposes.

TECHNICAL FIELD

The invention relates to a method for the production of a dental structure, such as a coping or crown, using a cavity that has a negative form of the structure, which is formed in an investment material (embedding mass) under use of a model that prescribes the shape of the cavity and which can be removed, wherein flowable lithium silicate glass ceramic is pressed into the cavity. The invention also relates to a dental ceramic structure, in particular a coping or crown of lithium silicate glass ceramic.

BACKGROUND

EP 1 543 797 A1 discloses a method for the production of a dental ceramic structure, in particular for pressing against, above, or around a framework of metal or ceramic, wherein flowable ceramic is pressed in a cavity that corresponds to the negative form of the corresponding structure in a muffle via at least one feed channel.

CH 668 699 A5 (=EP 0 231 773 A1) discloses a wax model provided with a ceramic stopper in a curable investment material. After the investment material has cured the stopper is removed so that a fill channel remains. The wax is burnt off through heating so that a mold cavity remains. A ceramic material is introduced into the fill channel and with the help of a highly-melt-resistant ceramic plunger the plastified ceramic material is pressed into the cavity.

The publications of I. L. Denry et. al., Enhanced Chemical Strengthening of Feldspathic Dental Porcelain, J Dent Res, October 1993, pages 1429 to 1433, and R. R. Seghi et. al., Effects of Ion Exchange on Hardness and Fracture Toughness of Dental Ceramics, The International Journal of Prosthodontics, Volume 5, No. 4, 1992, pages 309 to 314, disclose studies of composite ceramics which are comprised of feldspathic glass types in which leucite precipitates may be present. To increase strength, it was proposed to replace sodium ions by lithium ions and then to replace lithium ions by potassium ions in a two-step process. Smaller ions can also be replaced by rubidium ions. This enabled an increase in strength of up to a maximum of 80% if rubidium oxide was used. Rubidium, however, has the disadvantage that the heat expansion coefficient of the ceramics is increased.

A ceramic investment material to produce a casting mold and a method for its production are known from EP 2 062 665 A1. The investment material is produced from a ceramic particle mixture, a binding agent and a mixing fluid, containing at least one alkali polyphosphate.

DE 30 15 529 A1 discloses a method to improve the mechanical strength of dental porcelain. In this method a restoration is coated with enamel so that there is an exchange of alkali ions in the enamel. For this purpose the restoration is immersed in a bath of melted salt at a temperature between 200° C. and the transition point of the enamel.

The use of lithium silicate glass ceramic as a ceramic material has been proven in use in dental technology. Pellets derived from the glass ceramic can be pressed into the cavity by the above-described methods.

SUMMARY OF THE INVENTION

In one aspect, the present invention is directed to a method to produce a dental structure comprising the steps of: providing a cavity that has a negative shape of the structure, which is formed in an investment material using a model which prescribes the shape of the cavity and can be removed, wherein the model is enriched with one or more alkali compounds having alkali ions and/or the model is covered with a layer of material having alkali ions; pressing lithium silicate glass ceramic into the cavity to form a ceramic structure; and creating a surface compressive stress in the ceramic structure through the replacement of lithium ions by alkali ions.

In another aspect, the present invention is directed to a lithium silicate glass ceramic dental ceramic structure comprising a surface compressive stress that is created in the dental ceramic structure through the replacement of lithium ions by alkali ions.

In another aspect, the present invention is directed to a method for forming a lithium silicate glass ceramic pellet comprising the steps of: producing a melt that includes as starting components at least $SiO_2$, $Al_2O_3$, $Li_2O$, $K_2O$, at least one nucleating agent, at least one stabilizer, and at least one coloring metal oxide; and forming a pellet from the glass melt and subjecting the pellet to at least a first heat treatment W1 at a temperature $T_{W1}$ for a period of time $t_{W1}$, wherein $620°\,C. \leq T_{W1} \leq 800°\,C.$, and/or $1\text{ minute} \leq t_{W1} \leq 200\text{ minutes}$.

In yet another aspect, it is contemplated that the of the present invention has one or any combination of the following features: further comprising the step of forming the layer with which the model is covered with a melt having potassium ions from at least one salt selected from the group consisting of inorganic acids, organic acids or a combination of both; the inorganic acids and/or the organic acids are selected from the group consisting of nitrates, carbonates, acetates and chlorides; the one or more alkali compounds are in the form of one or more salts of inorganic acids and/or organic acids; the one or more salts of inorganic acids and/or organic acids are selected from the group consisting of nitrates, carbonates, acetates and chlorides; further comprising the step of applying the layer having a thickness D where $10\,\mu m \leq D \leq 100\,\mu m$; the percentage by weight of the alkali ions in the model or in the layer enveloping the model is in the range 0.5-10% by weight; the lithium silicate glass ceramic is produced from a glass melt that includes as starting components at least $SiO_2$, $Al_2O_3$, $Li_2O$, $K_2O$, at least one nucleating agent, at least one stabilizer, and at least one coloring metal oxide; the at least one nucleating agent is $P_2O_5$, the at least one stabilizer is $ZrO_2$, and the at least one coloring metal oxide is $CeO_2$ and/or $Tb_4O_7$; the glass melt includes the following starting components in percentage by weight:

| | |
|---|---|
| $SiO_2$ | 50-80, |
| at least one nucleating agent | 0.5-11, |
| $Al_2O_3$ | 0-10, |
| $Li_2O$ | 10-25, |
| $K_2O$ | 0-13, |
| $Na_2O$ | 0-1, |
| $ZrO_2$ | 0-20, |
| $CeO_2$ | 0-10, |
| $Tb_4O_7$ | 0-8, | optionally an oxide or a number of oxides of an earth alkali metal or a number of earth alkali metals from the group magnesium, calcium, strontium, barium 0-20,
optionally one or more additives selected from the group consisting of $B_2O_3$, $MnO_2$, $Fe_2O_3$, $V_2O_5$, $TiO_2$, $Sb_2O_3$, ZnO, $SnO_2$ and fluorides 0-6,
optionally one or more oxides of the rare earth metals with the atomic numbers 57, 59-64, 66-71, 0-5,
wherein the total sum is 100% by weight; the glass melt includes the following starting components in percentage by weight:

| | |
|---|---|
| $SiO_2$ | 52-70, |
| at least one nucleating agent | 3-8, |
| $Al_2O_3$ | 0.5-5, |
| $Li_2O$ | 13-22, |
| $K_2O$ | 0.5-8, |
| $Na_2O$ | 0-0.5, |
| $ZrO_2$ | 4-16, |
| $CeO_2$ | 0.5-8, |
| $Tb_4O_7$ | 0.5-6, | optionally an oxide or a number of oxides of an earth alkali metal or a number of earth alkali metals from the group magnesium, calcium, strontium, barium 0-20,
optionally one or more additives selected from the group consisting of $B_2O_3$, $MnO_2$, $Fe_2O_3$, $V_2O_5$, $TiO_2$, $Sb_2O_3$, ZnO, $SnO_2$ and fluorides 0-6,
optionally one or more oxides of the rare earth metals with the atomic numbers 57, 59-64, 66-71, 0-5,
wherein the total sum is 100% by weight; wherein the glass melt includes as starting components in percentage by weight the following:

| | |
|---|---|
| $SiO_2$ | 58.1 ± 2.0 |
| $P_2O_5$ | 5.0 ± 1.5 |
| $Al_2O_3$ | 4.0 ± 2.5 |
| $Li_2O$ | 16.5 ± 4.0 |
| $K_2O$ | 2.0 ± 0.2 |
| $ZrO_2$ | 10.0 ± 0.5 |
| $CeO_2$ | 0-3, |
| $Tb_4O_7$ | 0-3, |
| $Na_2O$ | 0-0.5, | wherein the total sum is 100% by weight; further comprising the step of forming one or more lithium silicate glass ceramic pellets from the glass melt and subjecting the lithium silicate glass ceramic pellet to at least a first heat treatment W1 at a temperature $T_{W1}$ for a period of time $t_{W1}$, wherein 620° C.$\leq T_{W1} \leq$ 800° C., and/or 1 minute$\leq t_{W1} \leq$ 200 minutes; the first heat treatment W1 is carried out in two steps, wherein the first step, the temperature $T_{St1}$ is 630° C.$\leq T_{St1} \leq$ 690° C. and/or in the second step, the temperature $T_{St2}$ is 720° C.$\leq T_{St2} \leq$ 780° C. and/or the heating rate $A_{St1}$ up to the temperature $T_{St1}$ is 1.5 K/minute$\leq A_{St1} \leq$ 2.5 K/minute and/or the heating rate $A_{St2}$ up to the temperature $T_{St2}$ is 8 K/minute$\leq T_{St2} \leq$ 12 K/minute; the one or more lithium silicate glass ceramic pellets after the first heat treatment W1 is subject to a second heat treatment W2 at a temperature $T_{W2}$ for a period of time $t_{W2}$, wherein 800° C.$\leq T_{W2} \leq$ 1040° C., and/or 5 minutes$\leq t_{W2} \leq$ 200 minutes; the alkali ions are selected from the group consisting of Na ions, K ions, Rb ions, of any combination thereof; a percentage of alkali ions replacing the lithium ions from a surface of the dental ceramic structure down to a depth of 10 μm is in the range 5-20% by weight, and/or at a depth between 8 and 12 μm from the surface the alkali ions are present in the range 5-10% by weight, and/or at a depth between 12 and 14 μm from the surface the alkali ions are present in the range 4-8% by weight, and/or at a depth of between 14 and 18 μm from the surface the range for the alkali ions is between 1-3% by weight; the dental ceramic structure is pressed against, over or around a dental technology framework of metal or ceramic, or any combination thereof.

DETAILED DESCRIPTION OF THE INVENTION

Figure 1:
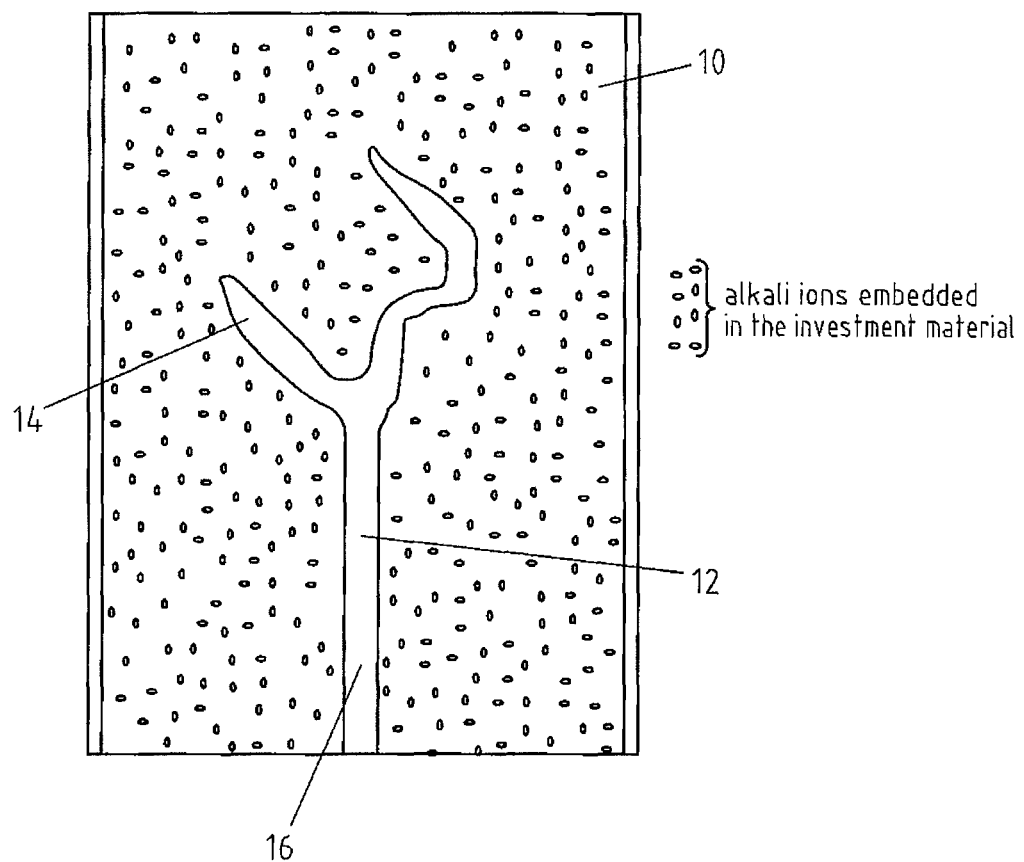
FIG. 1 shows a hardened investment material with a cavity.

The object of the present invention is to provide a method of the previously described type and a dental structure in which a lithium silicate glass ceramic is used as the ceramic, and which has a high strength after production of the structure. The increase in strength is to be achieved through simple measures compared to those for known lithium silicate glass ceramics. To achieve this aim it is in the main proposed that a compressive surface stress be created in the ceramic structure through the replacement of lithium ions by alkali ions, in that the investment material is enriched with alkali compounds and/or the model is covered with a layer of a material containing alkali ions.

In particular the invention provides for the use of a material containing potassium ions to form the layer that generates the surface compressive stress.

To bring about the replacement of lithium ions by larger ions to the necessary degree and therefore to achieve the desired increase in strength through the development of surface compressive stress, alkali compounds in the form of the salts of inorganic or organic acids, such as nitrates, carbonates, acetates or chlorides, are used and applied in a layer of thickness D where 10 μm$\leq$D$\leq$100 μm.

In particular, the percentage of the alkali ions, e.g., potassium ions, sodium ions, caesium ions or rubidium ions in the investment material/the model/the layer is in the range 0.5-10% by weight.

The model is in particular a wax model as known from ring (muffle) systems.

It was surprisingly found that when the lithium ions present in the form body of lithium silicate glass ceramic are replaced by larger alkali metal ions, a pre-stress and thus a surface compressive stress are generated, leading to a substantial increase in strength.

The invention is in particular characterized in that the ceramic material to be pressed, such as a pellet, is derived from a glass melt that has the following composition in percentage by weight:
  $SiO_2$ 50-80, preferably 52-70, especially preferred 56-61
  nucleating agent, such as P2O5, 0.5-11, preferably 3-8, especially preferred 4-7
  $Al_2O_3$ 0-10, preferably 0.5-5, especially preferred 1.5-3.2
  $Li_2O$ 10-25, preferably 13-22, especially preferred 14-21
  $K_2O$ 0-13, preferably 0.5-8, especially preferred 1.0-2.5
  $Na_2O$ 0-1, preferably 0-0.5, especially preferred 0.2-0.5
  $ZrO_2$ 0-20, preferably 4-16, in particular 6-14, especially preferred 8-12
  $CeO_2$ 0-10, preferably 0.5-8, especially preferred 1.0-2.5

Tb$_4$O$_7$ 0-8, preferably 0.5-6, especially preferred 1.0 to 2.0 optionally an oxide or a number of oxides of an earth alkali metal or a number of earth alkali metals from the group magnesium, calcium, strontium and barium 0-20, preferably 0-10, especially preferred 0-5, optionally one or more additives from the group B$_2$O$_3$, MnO$_2$, Fe$_2$O$_3$, V$_2$O$_5$, TiO$_2$, Sb$_2$O$_3$, ZnO, SnO$_2$ and fluorides 0-6, preferably 0-4 optionally one or more oxides of the rare earth metals with the atomic numbers 57, 59-64, 66-71, in particular lanthanum, yttrium, praseodymium, erbium, and europium, 0-5, preferably 0-3 wherein the total sum is 100% by weight.

"Optionally an oxide or a number of oxides" means that it is not absolutely necessary for one or more oxides to be contained in the glass melt.

The following composition in percentage by weight is in particular preferred:

| | |
|---|---|
| SiO$_2$ | 58.1 ± 2.0 |
| P$_2$O$_5$ | 5.0 ± 1.5 |
| Al$_2$O$_3$ | 4.0 ± 2.5 |
| Li$_2$O | 16.5 ± 4.0 |
| K$_2$O | 2.0 ± 0.2 |
| ZrO$_2$ | 10.0 ± 0.5 |
| CeO$_2$ | 0-3, preferably 1.5 ± 0.6 |
| Tb$_4$O$_7$ | 0-3, preferably 1.2 ± 0.4, |
| Na$_2$O | 0-0.5, preferably 0.2-0.5 | wherein the total sum is 100% by weight.

To derive the pellets the glass melt is poured into corresponding molds. After cooling to room temperature the pellet so derived is subject to at least a first heat treatment W1 at a temperature $T_{W1}$ for a period of time $t_{W1}$, wherein 620° C.≤$T_{W1}$≤800° C., in particular 650° C.≤$T_{W1}$≤750° C. and/or 1 minute≤$t_{W1}$≤200 minutes, preferably 10 minutes≤$t_{W1}$≤60 minutes.

This step results in the formation of nuclei and lithium metasilicate crystals.

In particular to obtain the final crystallization, in particular to produce lithium disilicate crystals or transform the metasilicate crystals into disilicate crystals it is provided for the lithium silicate glass ceramic blank after the first heat treatment W1 to undergo a second heat treatment W2 at a temperature $T_{W2}$ over a time $t_{W2}$, wherein 800° C.≤$T_{W2}$≤1040° C., preferably 800° C.≤$T_{W2}$≤900° C. and/or 2 minutes≤$t_{W2}$≤200 minutes, preferably 3 minutes≤$t_{W2}$≤30 minutes.

The following temperature values and heating rates are preferably chosen for the heat treatment steps leading to a pre-crystallization/final crystallization. With regard to the first heat treatment W1 it is in particular provided for a two-step approach, wherein a first holding stage is in the range 640° C. to 680° C. and a second holding stage is in the range 720° C. to 780° C. In each holding stage the heated blank is held at a temperature for a period of time; in the first stage this is preferably between 35 and 45 minutes and in the second stage preferably between 15 and 25 minutes.

A dental ceramic structure of the aforementioned type is characterized in particular in that a surface compressive stress is created in the dental ceramic structure through the replacement of lithium ions by alkali ions.

To create the surface compressive stress to the desired degree the alkali ions are Na, K and/or Rb ions.

A particular aspect of the invention is that the percentage of alkali ions replacing the lithium ions from the surface down to a depth of 10 μm is in the range 5 to 20% by weight, and/or at a depth between 8 and 12 μm from the surface the alkali ions are present in the range 5-10% by weight, and/or at a depth between 12 and 14 μm from the surface the alkali ions are present in the range 4-8% by weight, and/or at a depth of between 14 and 18 μm from the surface the range for the alkali ions is 1-3% by weight, wherein the percentage by weight of the alkali ions diminishes from layer to layer.

The invention is also characterized by a pellet that is derived by the method steps described above, to then be pressed to form a dental ceramic structure.

Further aspects, advantages and characteristics of the invention are derived not just from the claims and the characteristics to be drawn from them—alone and/or in combination—but also from the example embodiment below.

A starting composition as follows in percentage by weight

| | |
|---|---|
| SiO$_2$ | 59.8 |
| P$_2$O$_5$ | 5.5 |
| Al$_2$O$_3$ | 3 |
| Li$_2$O | 15.1 |
| K$_2$O | 1.2 |
| ZrO$_2$ | 9.7 |
| B$_2$O$_3$ | 2.7 |
| Na$_2$O | 0.2 |
| CeO$_2$ | 1.4 |
| Tb$_4$O$_7$ | 1.4 |
| Pr$_6$O$_{11}$ | 0.1 |
| Y$_2$O$_3$ | 0.4 |
| V$_2$O$_5$ | 0.3 |
| MnO$_2$ | 0.1 | was mixed in a drum mixer until a visually uniform mixture resulted.

The mixture was poured into a crucible of a platinum alloy of high temperature resistance and melted at a temperature of 1500° C. for 5 hours. The melt was then poured into molds to derive rectangular rods of the following dimensions: Length 15 mm, width 4.1 mm, height 1.2 mm. The rods were allowed to cool, removed and subjected to two heat treatment steps; in the first heat treatment step they were heated at a rate of 2 K/minute to 660° C. and held at this temperature for 40 minutes. They were then heated to 750° C. at a heating rate of 10 K/minute. The specimens were held at this temperature for 20 minutes. These heat treatments, designated as the first heat treatment step, influence nucleation and lithium metasilicate crystals are formed. The final crystallization was then carried out at a temperature of 850° C. for 8 minutes so that lithium disilicate crystals are formed or are formed from lithium metasilicate crystals. They are then cooled to room temperature. The three-point flexural strength of the rods was then determined by the method given in ISO 6872. For this purpose the specimens (rods) were mounted on two supports at a distance of 10 mm apart. A loading piston acted on the specimens between the rods, with the tip in contact with the specimen having a radius of 0.8 mm. The mean flexural strength value was 165 N/mm$^2$ with a standard deviation of 10 N/mm$^2$.

The same method was applied to obtain pellets for pressing into a cavity having the dimensions of a rod.

The investment material enveloping the cavity, comprising phosphate-bound cristobalite, was enriched with potassium ions with a percentage by weight of 1%. The investment material with the pellet was introduced into a pressing furnace. The plastified pellet was then pressed into the cavity at a pressing temperature of approx. 900° C. It was then cooled to room temperature and the lithium silicate glass ceramic body (specimen) removed and a three-point flexural strength determination carried out as described before. Ten such specimens were prepared and tested. The mean flexural strength value was 195 N/mm² with a standard deviation of 15 N/mm².

Micrographs of the specimens further showed that down to a depth of 10 µm to 15 µm from the surface the percentage of potassium ions was in the range 6.5-8% by weight.

In a second test series a wax body corresponding to the dimensions of the specimen was embedded in the investment material as a model, with the wax then burnt off in a furnace into which the investment material and wax body were introduced. The wax was enriched with potassium ions, with the potassium ions accounting for 1% by weight. A plastified lithium silicate glass ceramic pellet was then pressed into the cavity as described above and after cooling and removal of the specimen body the three-point flexural strength determined as given in ISO 6872. The mean flexural strength value for 10 specimens was 215 N/mm² with a standard deviation of 15 N/mm².

In a further test series the wax model was not enriched with potassium ions but instead the wax model was covered with a salt layer containing potassium ions. Potassium nitrate was used as the salt and the layer thickness was 100 µm.

After burning off the wax, as a result of which—as for test series 2—potassium ions diffused into the wall of the investment material delimiting the cavity, ten specimens were prepared as already described by pressing lithium silicate glass ceramic pellets.

The three-point measurements performed as already described yielded a mean flexural strength value of 230 N/mm² with a standard deviation of 20 N/mm².

Further details, advantages and features of the invention can be found not only in the claims, the features found therein—alone and/or in combination—but also in the following description of a preferred embodiment found in the drawings, in which:

FIG. 1 is a cross-sectional view of a hardened investment material 10 with a cavity 12. The upper part of the cavity 12 is the negative mold 14 of a dental structure to be produced. The lower part is a sprue channel 16 for pressing a plastified lithium silicate glass ceramic pellet into the negative mold 14. The negative mold 14 with the sprue channel 16 is formed after a respective positive model is positioned in a muffle mold and the interior space of the muffle mold is filled with investment material. After the investment material has hardened, the muffle mold is removed and the hardened investment material is heated, so that the material of the positive model can melt and flow out of the investment material. Into the cavity, hereby being formed, lithium silicate glass ceramic is then pressed. Respective positive models 18, 20 with sprue parts 22, 24 are shown in FIGS. 2 and 3.

Figure 2:
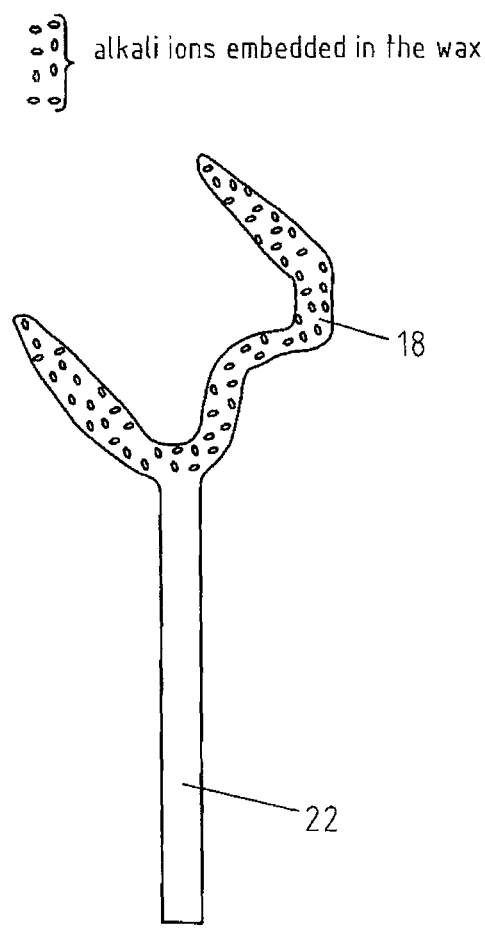
FIG. 2 shows a first embodiment of a positive model.
Figure 3:
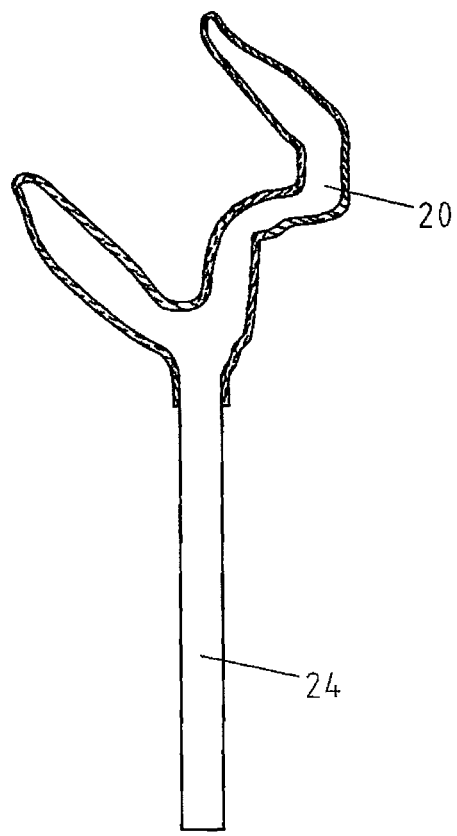
FIG. 3 shows a second embodiment of a positive model.

The positive model 18 of the dental structure to be produced according to FIG. 2 is made from wax or a similar material enriched with alkali compounds. According to FIG. 3, the positive model 20 is made from wax or similar material and covered with a layer of material containing alkali ions. The rod like parts 22, 24 corresponding to the sprue channel 16 of the negative mold are made from wax or similar material and must not contain alkali ions.

According to a further aspect of the invention, the investment material could also contain alkali compounds and ions, respectively, or alternative to the alkali compounds and/or ions of the positive models 18, 20, respectively.

To produce the dental structure, lithium silicate glass ceramic is pressed into the cavity 12. For this purpose, the investment material 10 is introduced into a furnace, in order to press the lithium silicate glass ceramic, after it has become flowable, into the cavity 12 via the sprue channel 16. As the material of the positive model 18, 20 and/or the investment material 10 contains alkali ions and compounds, respectively, lithium ions of the ceramic material are replaced by alkali ions with the result, that a surface compressive stress is created.

The invention claimed is:

1. A method to produce a dental structure comprising the steps of:
providing an investment mold having a cavity that has a negative shape of the dental structure, wherein the shape of the cavity is defined from a positive model formed in an investment material within the investment mold, wherein the positive model is covered with a layer of material that includes the alkali ions;
heating the investment mold so that at least a portion of the alkali ions in the layer of material covering the positive model is diffused into a wall of the cavity;
pressing lithium silicate glass ceramic into the cavity to form a ceramic structure; and
creating a surface compressive stress in the ceramic structure through replacement of lithium ions by alkali ions of a greater diameter between an exterior surface of the ceramic structure and the alkali ions diffused into the wall of the cavity;
wherein the layer is applied with a thickness D where 10 µm≤D≤100 µm; and
wherein the lithium silicate glass ceramic is derived from a glass melt that includes the following starting components in percentages by weight:

| | |
|---|---|
| SiO₂ | 52-70, |
| at least one nucleating agent | 3-8, |
| Al₂O₃ | 0.5-5, |
| Li₂O | 13-22, |
| K₂O | 0.5-8, |
| Na₂O | 0-0.5, |
| ZrO₂ | 4-16, |
| CeO₂ | 0.5-8, |
| Tb₄O₇ | 0.5-6, | greater than 0 but less than or equal to 20 of an oxide or a number of oxides of an earth alkali metal or a number of earth alkali metals from the group magnesium, calcium, strontium, barium,
greater than 0 but less than or equal to 6 of one or more additives selected from the group consisting of B₂O₃, MnO₂, Fe₂O₃, V₂O₅, TiO₂, Sb₂O₃, ZnO, SnO₂ and fluorides, and
greater than 0 but less than or equal to 5 of one or more oxides of the rare earth metals with the atomic numbers 57, 59-64, 66-71,
wherein the total sum is 100% by weight.

2. The method according to claim 1, wherein the percentage by weight of the alkali ions in the layer covering the positive model is in the range 0.5-10% by weight.

3. The method of claim 1, wherein the at least one nucleating agent is P₂O₅.

4. The method according to claim 1, further comprising the step of forming one or more lithium silicate glass ceramic pellets from the glass melt and subjecting the lithium silicate glass ceramic pellet to at least a first heat treatment W1 at a temperature Twi for a period of time $T_{w1}$, wherein 620° C.$\leq T_{w1} \leq$800° C., and/or 1 minute$\leq t_{w1} \leq$200 minutes.

5. The method according to claim 4, wherein the first heat treatment W1 is carried out in two stages, including a first holding stage having a temperature $T_{st1}$ wherein 630° C.$\leq T_{st1} \leq$690° C. and a heating rate $A_{st1}$ up to the temperature $T_{st1}$, wherein 1.5 K/minute$\leq A_{st1} \leq$2.5 K/minute; and a second holding stage having a temperature $T_{st2}$ wherein 720° C.$\leq T_{st2} \leq$780° C. and a heating rate $A_{st2}$ up to the temperature $T_{st2}$, wherein 8 K/minute$\leq T_{st2} \leq$12 K/minute.

6. The method according to claim 4, wherein the one or more lithium silicate glass ceramic pellets after the first heat treatment W1 is subject to a second heat treatment W2 at a temperature $T_{w2}$ for a period of time $t_{w2}$, wherein 800° C.$\leq T_{w2} \leq$1040° C., and/or 5 minutes$\leq t_{w2}$ 200 minutes.

7. The method of claim 1, wherein the layer of material with which the positive model is covered includes potassium ions and at least one salt selected from the group consisting of one or more inorganic acids and one or more organic acids.

8. The method of claim 7, wherein the layer of material with which the positive model is covered further alkali compounds in the form of one or more salts of inorganic acids and/or organic acids that are selected from the group consisting of nitrates carbonates, acetates and chlorides.

* * * * *